US00PP16257P2

(12) United States Plant Patent
Laviana

(10) Patent No.: US PP16,257 P2
(45) Date of Patent: Feb. 14, 2006

(54) ***TRICYRTIS* PLANT NAMED 'RASPBERRY MOUSSE'**

(50) Latin Name: *Tricyrtis hirta*
Varietal Denomination: Raspberry Mousse

(75) Inventor: Marc R. Laviana, Kensington, CT (US)

(73) Assignee: Sunny Border Nurseries, Inc., Kensington, CT (US)

( * ) Notice: Subject to any disclaimer, the term of this patent is extended or adjusted under 35 U.S.C. 154(b) by 60 days.

(21) Appl. No.: 10/989,919

(22) Filed: Nov. 8, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
(74) *Attorney, Agent, or Firm*—Penny J. Aguirre

(57) ABSTRACT

A new cultivar of *Tricyrtis hirta* 'Raspberry Mousse' characterized by its red flowers that are spotted and marked with deep purple and borne in a thick column on arching stems.

1 Drawing Sheet

Genus and species: *Tricyrtis hirta.*
Cultivar: 'Raspberry Mousse'.

BACKGROUND OF THE INVENTION

The present invention relates to a new and distinct cultivar of *Tricyrtis hirta* and will be referred to hereafter by its cultivar name, 'Raspberry Mousse'. 'Raspberry Mousse' represents a new Japanese toad lily, an herbaceous perennial grown for landscape use.

The inventors discovered the new cultivar, 'Raspberry Mousse', as a naturally occurring branch sport of *Tricyrtis hirta* 'Miyazaki' (not patented) in a block of nursery stock nursery in Kensington, Conn. in September of 2002.

The new Toad Lily was selected as unique for its dark red-purple flowers. 'Raspberry Mousse' has similar characteristics to its parent, 'Miyazaki', in producing flowers that are borne in a thick column along the upper side of arching stems, however the tepals of 'Miyazaki' are white with purple spots whereas the tepals of 'Raspberry Mousse' are red with purple spots.

Asexual reproduction of the new cultivar was first accomplished by in vitro propagation in Kensington, Conn. in December of 1992 by the inventors. The characteristics of this cultivar have been determined to be stable and are reproduced true to type in successive generations.

SUMMARY OF THE INVENTION

The following traits have been repeatedly observed and represent the characteristics of the new cultivar after two years of observation. These attributes in combination distinguish 'Raspberry Mousse' as unique from all other selections and forms of *Tricyrtis hirta* known to the inventors.

1. Flowers with tepals that are red with dark purple spots and markings, the tepals of the parent plant, 'Miyazaki' are white with dark purple spots.
2. Flowers are borne in a column on the upper surface of cascading stem from late August to late September in Kensington, Conn.
3. Vigorous growing rate once roots are established.
4. Cold hardy at least to USDA Zone 5.
5. Grows to a height and spread of 60 cm.

BRIEF DESCRIPTION OF THE DRAWING

The accompanying photograph depicts a flower on a three-year-old plant of 'Raspberry Mousse' as grown outdoors in bright shade in Kensington, Conn. The colors in the digital photograph are as close as possible with the photographic techniques utilized and the color chart readings in the botanical description most accurately describe the new *Tricyrtis.*

BOTANICAL DESCRIPTION OF THE PLANT

The following is a detailed description of the new cultivar as grown in a one-gallon container outdoors for two years from a single rhizome division of 'Raspberry Mousse' in Kensington, Conn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Raspberry Mousse' is a cultivar of *Tricyrtis hirta.*
Parentage: Branch sport of *Tricyrtis hirta* 'Miyazaki'.
General description:
- *Blooming period.*—Late August to late September.
- *Plant habit.*—Herbaceous, clump-forming perennial, habit is upright with pendant stems with flowers arising on upper side of the stems.
- *Height and spread.*—About 60 cm in height and spread.
- *Hardiness.*—Tested to USDA Zone 5.
- *Culture.*—Grows best in moist, well-drained soil in shade or partial shade.
- *Diseases and pests.*—*Tricyrtis hirta* is relatively disease free, no susceptibility or resistance to diseases or pests has been observed for 'Raspberry Mousse'.
- *Root description.*—Fleshy roots arising from short rhizomes.

Growth and propagation:
- *Propagation.*—Tissue culture and division.
- *Growth rate.*—Moderately vigorous.

*Time required for root development.*—Rooted transplants from tissue culture fully develop and harden-off in a 32-cell liner in about 6 to 8 weeks in a greenhouse, a one-gallon container will finish in 12 to 14 from a 32-cell liner when grown outdoors in summer.

Stem description:

*Shape.*—Round.

*Stem color.*—144C to 144D, basal portion and occasionally the upper surface of the stems are tinted purple N77A.

*Stem size.*—Main stems; about 7 mm in diameter at base tapering to 2 to 3 mm at apex, up to about 40 cm in length, Side branches; up to 4 mm at node tapering to 2 to 3 mm at apex, up to about 26 cm in length.

*Stem surface.*—Glabrous base, moderately covered with fine white hairs (noticeable), about 1 mm in length.

*Branching.*—3 primary branches on a one-gallon plant, 2 to 3 secondary branches/main branch if un-pinched.

*Internode length.*—1 to 3.0 cm.

Foliage description:

*Leaf shape.*—Lanceolate.

*Leaf division.*—Simple.

*Leaf base.*—Cordate, clasping around entire stem, appears perfoliated.

*Leaf apex.*—Acuminate.

*Leaf venation.*—Camptodrome, almost parallel, typically 3 pairs of veins surrounding midrib. Slightly recessed on upper foliage, raised on lower surface, color matching the color of foliage on lower surface and distal portion of upper surface, color is 144D on basal portion of upper surface.

*Leaf margins.*—Entire, fine white hairs.

*Leaf attachment.*—Clasping, appearing perfoliated.

*Leaf arrangement.*—Alternate.

*Leaf surface.*—Upper; scabrous, imparting a slight whitish cast. Lower; glabrous.

*Leaf color.*—Newly formed leaves, upper and lower surface: between 144A and 144B, Mature leaves, upper surface; 146A with undertones of 144A, lower surface; 146B, leaf color becomes primarily 144A with cooler temperatures in fall.

*Leaf size.*—Up to about 11 cm in length, 4 cm in width.

*Leaf quantity.*—Up to about 35 per stem with two secondary branches.

Flower description:

*Inflorescence type.*—Borne singularly or in pairs at leaf nodes with the terminal flowers borne in clusters of 3 to 5 flowers.

*Lastingness of inflorescence.*—Determinate, individual blooms last approximately 1 week, blooms open randomly along stem with a total bloom time of about 4 weeks.

*Flower fragrance.*—None.

*Perianth form.*—Open bell-shaped, comprised of 6 un-fused tepals with the 3 outer tepals having a saccate base.

*Flower aspect.*—Held upward on upper surface of cascading stems, tepal tips are reflexed.

*Flower size.*—About 3 cm in depth, about 4 cm in width.

*Flower number.*—10 to 16 per stem, about 60 blooms on a one gallon plant with 3 main stems.

*Tepal color.*—(Opening and mature), upper surface; base of 53B with deep purple spots and marking covering from 20 to 50% of the leaf surface N79A to 79B with a small patch (2 mm in width and 4 mm in length) of yellow-orange 16A near the base, lower surface; 53B with shadows of upper surface markings N79D with saccate base 155D.

*Tepal surface/appearance.*—Upper surface is glabrous with velvety markings, lower surface is waxy.

*Tepal size.*—Average of 2.5 cm in length, inner tepals about 5 mm in width, outer tepals about 8 mm in width, saccate base on outer tepals is 3 mm in diameter.

*Tepal apex.*—Inner tepals acute, outer tepals acuminate.

*Tepal base.*—Inner tepals triangular, outer tepals saccate.

*Tepal margin.*—Entire.

*Buds size.*—Up to 2.5 cm in length, up to 9 mm in width.

*Bud color.*—Emerge 144A with apex of 59A, changes to 144D with apex and petal margins of 59A.

*Bud shape.*—Ovate becoming Oblong before opening with 3 globose sacs at base; 3 mm in diameter, 155C in color.

*Peduncles.*—Arise from leaf node at center of leaf attachment, about 1 cm in length, about 2 mm in width, 144C in color, hairy surface.

Reproductive organs:

*Gynoecium.*—Pistil; 1, 2.8 cm in length and 1.8 cm in width, showy, style; 4 mm in length and 1.5 mm in width, 155C in color, stigma; comprised of 3 recurved bifid branches, 155C in color with spots of 71A, branches recurved, branches are about 1 cm in length and 1 mm in width, globose receptors on margins (translucent appearance), ovary; superior, 3-celled, 1 cm in length and 3 mm in width, 150C in color.

*Androecium.*—6 stamens; showy, exserted, appressed and completely surrounding ovary and style, un-fused, filaments; 3 mm in width at base tapering to 0.3 mm at anther attachment, color is a base of N155C with purple spots 77B and overlaid with N74D, waxy in appearance, recurved at tip to hold anthers downward, anthers; 6 mm in length and 2 mm in width, attachment is versatile, 76B in color, pollen; moderately abundant, very fine, 76C in color, dehiscence is longitudinal.

*Fruit and seeds.*—3 sided septicidal capsule, about 2.5 cm in length and 5 mm in width, 144A in color, seeds are numerous, flat and very small.

I claim:

1. A new and distinct cultivar of *Tricytis hirta* plant named 'Raspberry Mousse' substantially as herein illustrated and described.

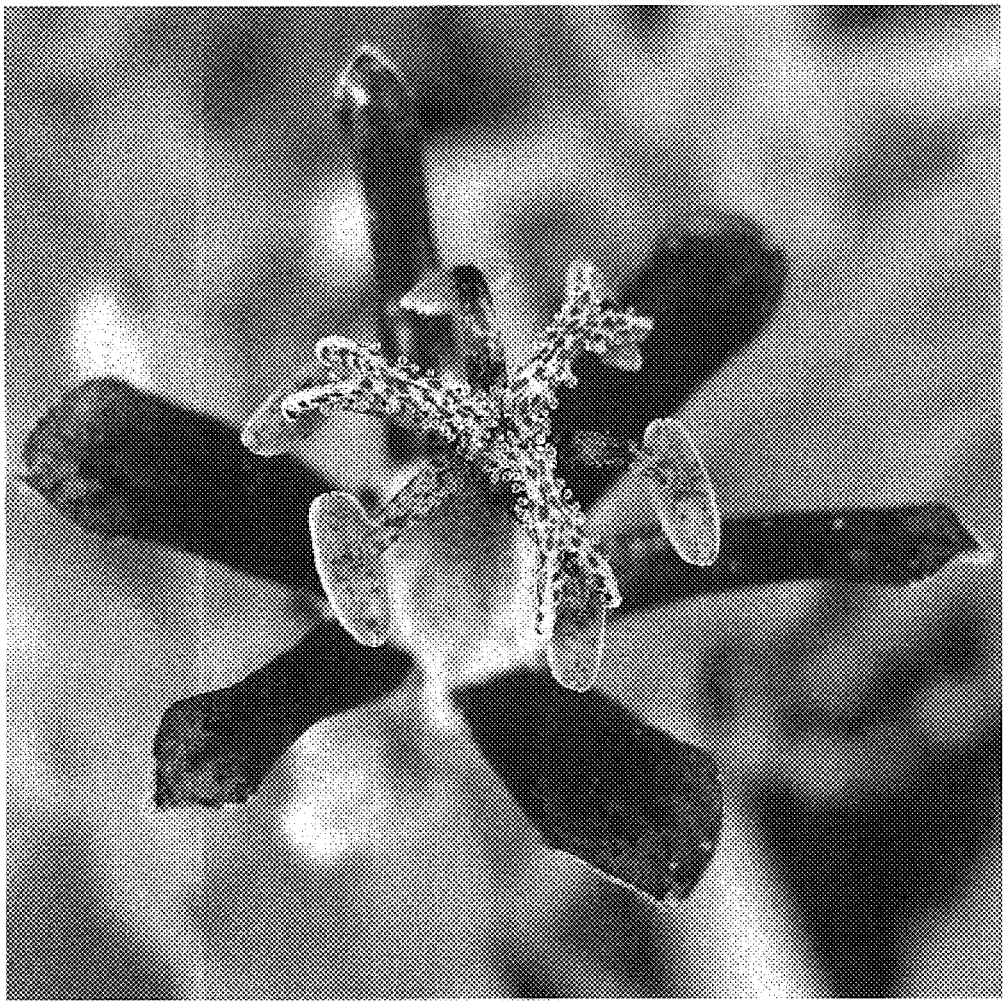

* * * * *